United States Patent

Folsom

[11] Patent Number: 5,888,218
[45] Date of Patent: Mar. 30, 1999

[54] IMPLANT MICRO SEAL

[75] Inventor: Aubrey Clint Folsom, Pelham, Ala.

[73] Assignee: Folsom Metal Products, Pelham, Ala.

[21] Appl. No.: 826,490

[22] Filed: Mar. 27, 1997

[51] Int. Cl.[6] .................................................. A61F 2/28
[52] U.S. Cl. ............................ 623/16; 433/172; 433/181; 433/182
[58] Field of Search ..................................... 433/172–174, 433/181, 182; 623/16, 18

[56] References Cited

U.S. PATENT DOCUMENTS

| | | | |
|---|---|---|---|
| 4,657,510 | 4/1987 | Gittleman | 433/174 |
| 5,071,350 | 12/1991 | Niznick | 433/174 |
| 5,106,300 | 4/1992 | Voitik | 433/173 |
| 5,120,222 | 6/1992 | Sulc | 433/181 |
| 5,125,840 | 6/1992 | Durr et al. | 433/173 |
| 5,145,371 | 9/1992 | Jörneús | 433/174 |
| 5,195,891 | 3/1993 | Sulc | 433/173 |
| 5,213,500 | 5/1993 | Salazar et al. | 433/173 |
| 5,302,125 | 4/1994 | Kownacki et al. | 433/173 |
| 5,344,457 | 9/1994 | Pilliar et al. | 623/16 |
| 5,376,004 | 12/1994 | Mena | 433/174 |
| 5,417,570 | 5/1995 | Zuest et al. | 433/173 |
| 5,447,434 | 9/1995 | Shaw | 433/173 |
| 5,667,384 | 9/1997 | Sutter et al. | 433/173 |

FOREIGN PATENT DOCUMENTS 6-237944 A  8/1994  Japan ........................ 623/16

*Primary Examiner*—Michael J. Milano
*Assistant Examiner*—Tram A. Nguyen
*Attorney, Agent, or Firm*—Veal & Associates

[57] ABSTRACT

An osteo-integrated implant utilizes a metal seal formed on the outer diameter of the implant components spaced axially from the annular seat or junction of the components. The sealing surface of one component is machined on the internal diameter of a counter-bored cylindrical member extending over the junction to engage the outer diameter of the other component. The mating surface is formed on the outer diameter and is machined such that an interference fit exists between the two surfaces when the abutment is fully seated in the implant. The design allows for both radial and axial micro motion without compromise to the sealing effectiveness.

1 Claim, 1 Drawing Sheet

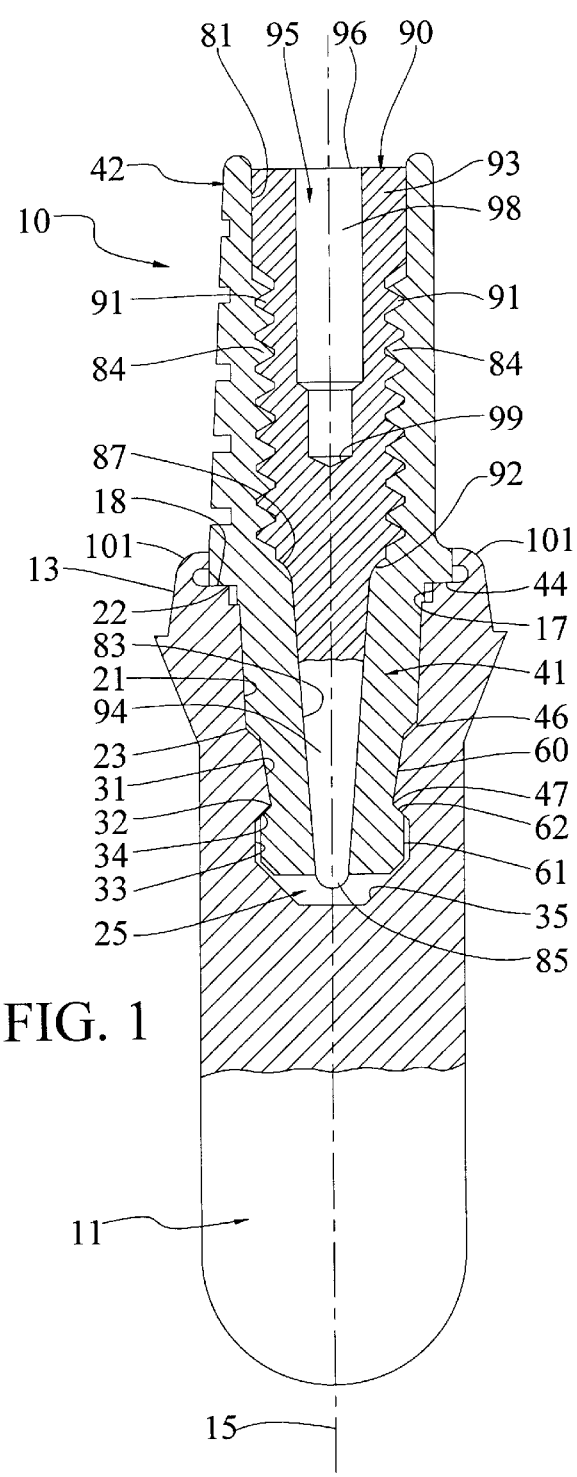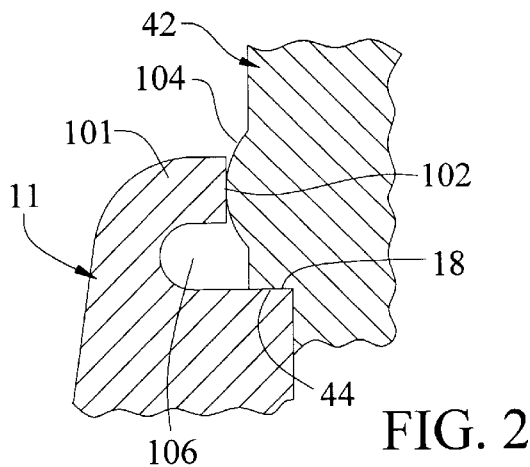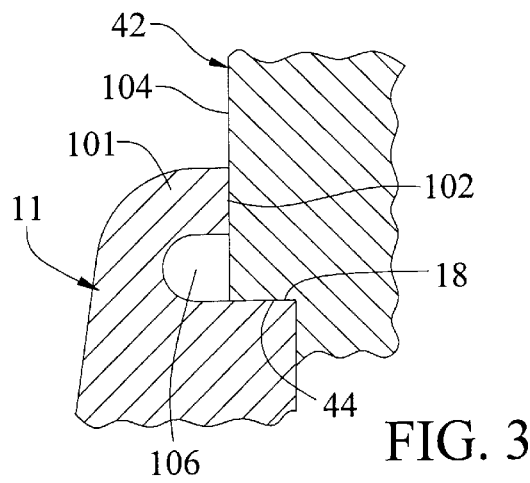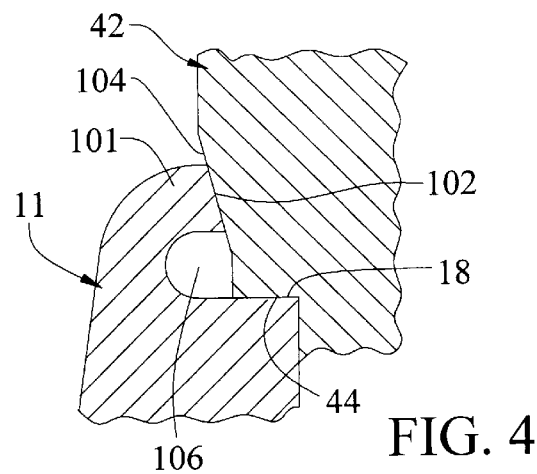

IMPLANT MICRO SEAL

FIELD OF THE INVENTION

The present invention relates to the field of osteo-integrated implants, and particularly to implants wherein an implant anchor and an implant abutment are utilized in conjunction with a prosthesis. More particularly, the present invention relates to sealing of the junction of anchor and abutment.

BACKGROUND OF THE INVENTION

In the field of Osteo-integrated implants, more specifically cemented implants, tissue inflammation and bone loss occur near the junction between the implant and the abutment. This problem results from bacteria living in the gap between the implant and abutment. The gap is too small to allow blood from the host tissue to enter and destroy the bacteria with antibodies. As the bacteria thrive and colonize, they issue toxins which irritate tissue and destroy crestial bone around the implant. Previous attempts to solve the problem involve the use of elastomeric coatings and gaskets at the junction. These attempts have failed due to the continuous micro motion from chewing forces transmitted through the implant abutment interface which destroy the elastomer over time and render this type of seal non-functional. Accordingly, a need exists for a means to seal the junction in such a manner as to substantially preclude the growth of bacteria between implant components.

SUMMARY OF THE INVENTION

It is the principal object of the present invention to improve the efficacy of surgical implants by reducing the loss of crestial bone about implant sites.

It is a further object of the present invention to reduce the instances of pain and inflammation of tissues surrounding implant sites.

It is in the furtherance of the foregoing objects that this invention has as its object the efficacious sealing of the junction between implant anchors and the abutment structures used therewith.

These and further objects and advantages of the present invention are accomplished using a combination of elements novel in the field of osteo-integrated implants. The present invention utilizes a metal seal formed on the outer diameter of the implant components spaced axially from the annular seat or junction of the components. The sealing surface of one component is machined on the internal diameter of a counter-bored cylindrical member extending over the junction to engage the outer diameter of the other component. The mating surface formed on the outer diameter is machined such that an interference fit exists between the two surfaces when the abutment is fully seated in the implant. The design allows for both radial and axial micro motion without compromise to the sealing effectiveness.

BRIEF DESCRIPTION OF THE DRAWINGS

Apparatus embodying features of my invention are depicted in the drawing appended hereto which form a portion of this disclosure and wherein:

FIG. 1 is a sectional view through a preferred implant system which incorporates the invention;

FIG. 2 is an exaggerated partial view of the sealing surfaces of the present invention in one embodiment;

FIG. 3 is an exaggerated partial view of the sealing surfaces of the present invention in a second embodiment; and, FIG. 4 is an exaggerated partial view of the sealing surfaces of the present invention in a third embodiment;

DESCRIPTION OF THE PREFERRED EMBODIMENTS

Referring to the drawings for a better understanding of the function and structure of the invention, the present invention is illustrated with respect to a specific implant system although other systems may be as readily adaptable to the teachings. In the illustrated system as shown in FIG. 1, implant system 10 is comprised of three main components; an implant anchor 11, an abutment 42, and a locking pin 90. The combination of these elements is particularly adapted to the field of dental implant prosthetics, however it should be understood that the scope of the invention includes other orthopedic implants. Implant 11 is generally osseointegrated into a targeted human bone as, for example, a human jaw bone. The structure of the inferior end of the implant anchor 11 may be a root-form implant, a blade-form implant, or a sub-periodontal implant. The implant may be also manufactured in any of the following forms to promote bone growth and regeneration: threaded screw-type, cylindrical, stepped surface, hollow cylindrical baskets, or blades. The insertion end of the implant anchor 11 may be configured to be self tapping or tapered to mate with a pre-tapped hole in the jaw bone.

Internally, the implant 11 is conformed for mating engagement with abutment 42. The attachment or coronal end 13 of implant 11 includes a constant diameter annulus 17 circumscribing an axial bore. A bearing surface 18, perpendicular to the axis 15 of the implant is formed by the constant diameter annulus 17, and circumscribes a internally recessed frusto-conic section 21 which tapers from a maximum diameter 22 at the bearing surface 18 to a minimum diameter 23. The internally recessed conic section 21 may be machined or otherwise formed such that a plurality of longitudinally oriented splines and flutes are formed in the cone surface. A smooth conic portion 31 begins at the minimum spline diameter 23 and tapers down to the minimum cone diameter 32. An annular groove 33 is machined below the smooth conic portion 31 to form a retention surface 34. The bore 25 terminates subjacent groove 33 with a frusta conical recess 35 for receiving the lower tip 85 of locking pin 90 once fully inserted.

As shown in FIG. 1 the superior end of the abutment has a plurality of circumferentially oriented grooves and a beveled surface for use as a leverage bearing surface and for prosthetic alignment. The abutment 42 serves to connect the prosthesis to the implant 11 and the grooves facilitate cementation of the prosthesis to the implant as is well known in the art. The abutment forms a lower annular surface 44 which is formed for cooperative support on bearing surface 18.

A mating protrusion 41 is circumscribed by the annular surface 44 and tapers toward axis 15 from below the surface 44 to a minor diameter 46. The protrusion 41 includes several surface features conforming to the interior surface features of implant bore 25. The protrusion 41 is machined such that the tapered surface has formed thereon a plurality of alternating splines and flutes, which register with the splines and flutes of the recessed conic section 21. A smooth frusta-conical surface 60 begins at the minor diameter 46 of the splines and tapers down to a reduced diameter 47. An annular protruding lip 61 is machined below the smooth surface 60 and has a retention surface 62. The lip 61 is designed to register with groove 33 such that the abutment retention surface 62 registers against implant retention surface 34. A downwardly opening vertical slot (not shown) is milled or otherwise formed through the abutment external protrusion 41 such that two symmetrical segments are formed.

The midsection of an axial bore 81 formed in abutment 42 is threaded at 84 for engagement with locking pin 90, and a curved surface 87 formed below the threaded receptacle. The bore 81 also has a reduced transition diameter section 83 extending to the inferior end.

Referring again to FIG. 1, it may be seen that locking pin 90 engages the abutment 42 for the purpose of locking the abutment protrusion 41 into the implant 11. The locking pin 90 is generally cylindrical shaped and has a threaded midsection 91 which threadably engages the abutment threads 84. The superior portion of the locking pin 90 includes a constant diameter section 93 connected to the threaded mid-section 91 via a transition section 101. The lower or inferior portion of the pin 90 has a reduced diameter section 94, which terminates at a lower conical tip 85. A curved retention surface 92 is machined below the threaded receptacles 91 and serves to form a cooperative surface with the bearing surface 87 of the abutment bore. An axial bore 95 is formed from the top portion of the superior end of the pin and terminates within the threaded section 91 at 99. The bore 95 includes a hexagonally shaped inner surface section 98 starting at 97, and the uppermost section of the bore 95 has a smooth inner surface from a position at 97 to 96 as shown.

As may be seen from the foregoing, the mating surfaces on the exterior of the abutment protrusion 41 and the implant bore 25 are positioned such that the abutment can be seated with precision relative to the implant 11, thereby facilitating alignment of a prosthesis installed on the abutment. Further, the interaction of the cooperative splines and flutes resists torsional loads and prevents angular movement of the abutment relative to the implant without inducing stress raising discontinuities in the interfaces. Thus, torsional loading is not concentrated as may occur with rectangular keys or hex connections. It will also be appreciated that the surface features of the bore 25 provide a means for applying torque to the implant with an insertion tool having a cooperative surface to facilitate seating of the implant within the jaw bone initially.

When the abutment 42 and implant 11 are properly mated, a cooperative interface resistant to axial and angular movement is formed by the abutment retention surface 62 and the implant retention surface 34, and the mated splines and flutes. When the locking pin 90 is fully inserted into the abutment 42, the segmented portions of the abutment protrusion 41 is prevented from deforming, thereby locking the abutment in place.

The foregoing description relates to the specific implant system claimed in commonly owned application Ser. No. 08/762,881, whereas the following described improvements may be utilized in any of a number of implant systems wherein the anchor 11 and abutment 42 form a junction as shown at bearing surface 18. The invention claimed herein is a metal seal formed on the outer diameter of one of the components forming the junction. That is to say the seal may be formed on the outer diameter of the anchor 11 or the abutment 42, although the abutment may be preferred.

Referring again to FIG. 1, note that bearing surface 18 is circumscribed by a counter-bored cylindrical protrusion 101 which extends upwardly until it terminates to form an annular seal surface 102. The seal surface 102 is actually machined on the inner diameter of protrusion 101 slightly above the plane of surface 18 which defines the external junction between the abutment and anchor in prior art systems. Seal surface 102 is narrow relative to the length of protrusion 101. Abutment 42 has formed on its exterior surface a sealing area 104 extending upwardly and circumscribing surface 44. When the abutment is fully seated on the anchor sealing surface 102 engages the mating surface at 104. The surfaces are machined such that an interference fit exists between the two surfaces, thereby forming a metal to metal seal at the abutment outside diameter and protrusion inside diameter. It will be noted that a recess 106 is formed intermediate surface 102 and surface 44 within which an elastomeric member such as an O-ring may be optionally secured, however, such a seal is redundant in view of the metal to metal seal which allows for both radial and axial micromovement without compromising seal effectiveness.

It should be noted that protrusion 101 may be formed on abutment 42 and engage the outer surface of the anchor. Further, the specific shapes of the milled surfaces may vary as shown in FIG.'S 2 to 4. That is to say one surface may be arcuate and interfere with a planar surface formed on the other member as shown in FIG. 2. Both surfaces may be cylindrical with interfering outer and inner diameters as in FIG. 3, or both may be conic and interfering as shown in FIG. 4.

While I have shown my invention in one form, it will be obvious to those skilled in the art that it is not so limited but is susceptible of various changes and modifications without departing from the spirit thereof. It should also be understood that although much of the foregoing description was directed to a dental implant, the scope of the invention includes other types of orthopedic implants well known to those skilled in the art.

What I claim is:

1. In an implant system wherein an implant is osseointegrated into a bone and an abutment is inserted into a cylindrical counter bore in said implant forming an annular junction therebetween at the interface of a bearing surface formed on said implant transversely of said counter bore and an annular surface formed on said abutment the improvement comprising:

a. a cylindrical protrusion formed on one side of said junction and circumscribing said junction;

b. a machined sealing surface defining an inner diameter of said cylindrical protrusion on an opposite side of said junction; and, c. an annular interference surface formed on an opposite side of said junction such that proper insertion of said abutment into said implant forms an interference seal between said machined surface and said interference surface wherein said interference seal is formed between a cylindrical surface and a spherical surface.

\* \* \* \* \*